US00PP11076P

United States Patent [19]

Yu-Lin

[11] Patent Number: Plant 11,076

[45] Date of Patent: Oct. 5, 1999

[54] APPLE TREE NAMED 'HUASHUAI'

[75] Inventor: Wang Yu-Lin, Auckland, New Zealand

[73] Assignee: Fruit Industry Plant Improvement Agency, Hastings, New Zealand

[21] Appl. No.: 08/982,984

[22] Filed: Dec. 2, 1997

[51] Int. Cl.[6] ..... A01H 5/00

[52] U.S. Cl. ..... Plt./161

[58] Field of Search ..... Plt./34.1, 161

[56] References Cited

PUBLICATIONS

UPOV CD–ROM, Apple tree named 'Huashuai', PBR APP124, New Zealand, 1996.

UPOV CD–ROM, Apple tree named 'Huashuai', PBR 96–971, Canada, 1996.

UPOV CD–ROM, Apple tree named 'Huashuai', 96273, Australlia, 1996.

UPOV CD–ROM, Apple tree named 'Huashuai', PBR 9274, Japan, 1996.

*Primary Examiner*—Howard J. Locker

*Assistant Examiner*—Melissa L. Kimball

*Attorney, Agent, or Firm*—Klarquist Sparkman Campbell Leigh & Whinston, LLP

[57] ABSTRACT

A new and distinct variety of apple named 'Huashuai' characterized by: (1) a tree of medium vigor that blooms in mid-season and has spreading branches due to early and heavy fruit production; (2) deep red buds opening to a blossom having white petals tinged with a light pink; (3) fruit having a variable conical to ovate shape with five points on the calyx end, a medium to long stem, a calyx bowl that is deeper than that of 'Fuji', creamy white flesh, a sweet flavor with low acidity and with a mild distinguishing aroma, and a yellowish green to golden yellow skin color overlaid with a very attractive pink to red blush made up of fine bright crimson red stripes; and (4) dark green leaves with sinuate, serrate margins, prominent veins on the upper side, and medium buff/green pubescence covering the underside.

6 Drawing Sheets

BACKGROUND OF THE INVENTION

The present invention comprises a new and distinct variety of apple tree, referred to by the varietal name 'Huashuai'. The English translation of the varietal name Huashuai is 'Chinese Marshal'.

The original tree of the new variety was discovered in 1989 in a cultivated area in Zhengzhou, Henan province, People's Republic of China. 'Huashuai' is a selection from a controlled cross of 'Fuji'×'Bisbee'. Throughout this description, 'Fuji' refers to the standard, unpatented 'Fuji' variety of apple tree, and 'Bisbee' refers to the 'Bisbee' red delicious apple cultivar (U.S. Plant Pat. No. 1,564) sometimes sold under the trademark STARKCRIMSON®.

Trees of 'Huashuai' were observed at the Washington State University Research Station at Prosser, Wash., in test plots of the Pacific Northwest Fruit Tester's Association in Selah, Wash., and were compared to 'Fuji'and 'Bisbee' trees.

This invention has not been observed under all possible environmental conditions. However, the following combination of traits has been repeatedly observed in asexually propagated progeny and are determined to be the basic characteristics of this invention, which in combination distinguish 'Huashuai' as a new and distinct variety: (1) a tree of medium vigor that blooms in mid-season and has spreading branches due to early and heavy fruit production; (2) deep red buds opening to a blossom having white petals tinged with a light pink; (3) fruit having a variable conical to ovate shape with five points on the calyx end, a medium to long stem, a calyx bowl that is deeper than that of 'Fuji' trees, creamy white flesh, a sweet flavor with low acidity and with a mild distinguishing aroma, and a yellowish green to golden yellow skin color overlaid with a very attractive pink to red blush made up of fine bright crimson red stripes; and (4) dark green leaves with sinuate, serrate margins, prominent veins on the upper side, and medium buff/green pubescence covering the underside.

Asexual reproduction by budding at Prosser, Wash. and elsewhere shows that these characteristics are established and transmitted through succeeding asexual propagations.

BRIEF DESCRIPTION OF THE PHOTOGRAPHS

DETAILED DESCRIPTION

The following is a detailed description of the invention based on plants grown under orchard practices at a Washington State University research plot at Prosser, Wash., and a test plot at a farm near Prosser, Wash. All trees were bearing on the dwarfing unpatented 'Malling 26' rootstock.

Color references employ terms of ordinary dictionary significance except where reference is made to The Royal Horticultural Society Colour Chart (R.H.S.). It should be understood that colors vary depending upon factors such as growing and lighting conditions.

All trees of the new variety, insofar as I have been able to observe them, are identical in all the characteristics described below.

Species: *Malus pumila.*

Parentage: 'Fuji'×'Bisbee'.

Propagation: Holds to distinguishing characteristics through succeeding propagation by budding.

Dates of first and last picking: Varies with growing season. In 1994 and 1995, fruit was picked in the second week of September. In 1996, fruit was picked September 8–14. The mid-season harvest coincides with 'Bisbee'.

Tree:

*Vigor.*—Medium vigor (less vigorous than 'Fuji', more similar to a spur-type 'Bisbee') with early and heavy bearing.

Figure 1:
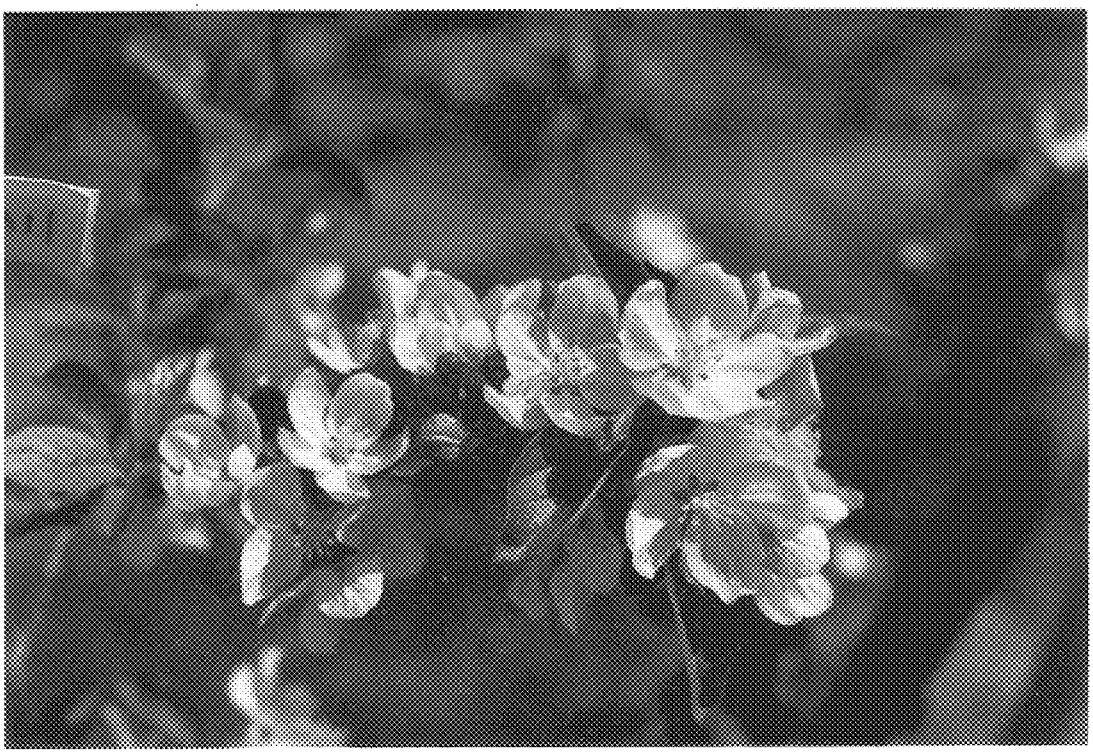
FIG. 1 is a view of blossoms of 'Huashuai'.
Figure 2:
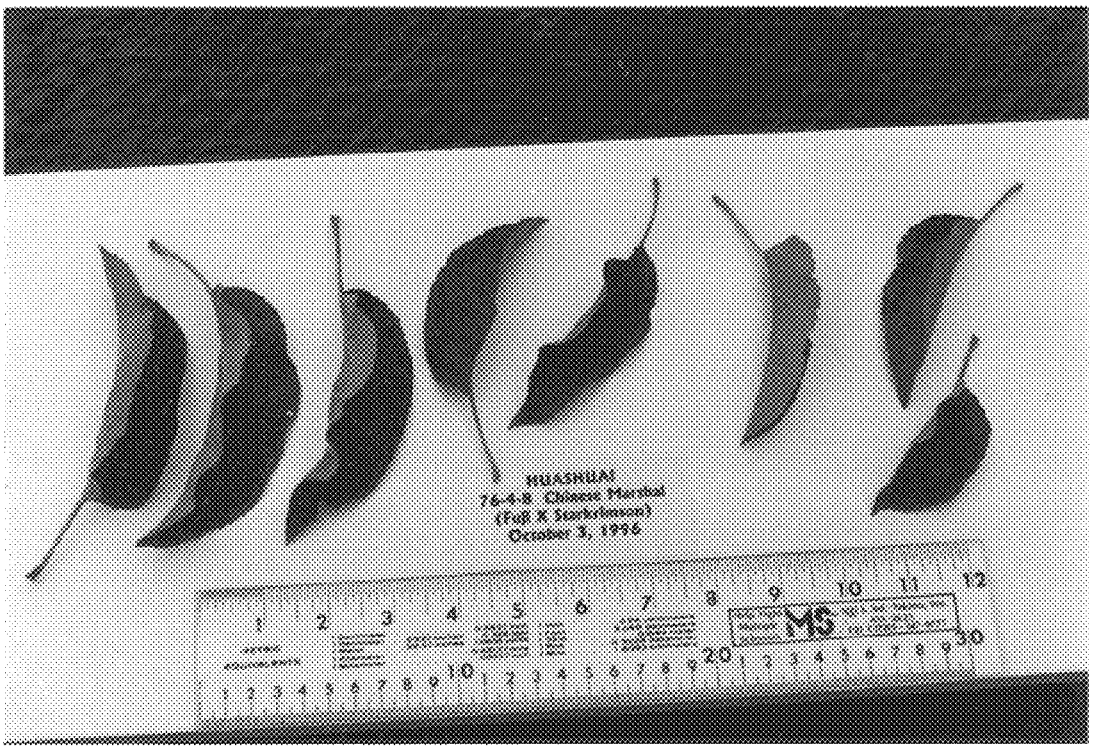
FIG. 2 is a view of leaves of 'Huashuai'.
Figure 3:
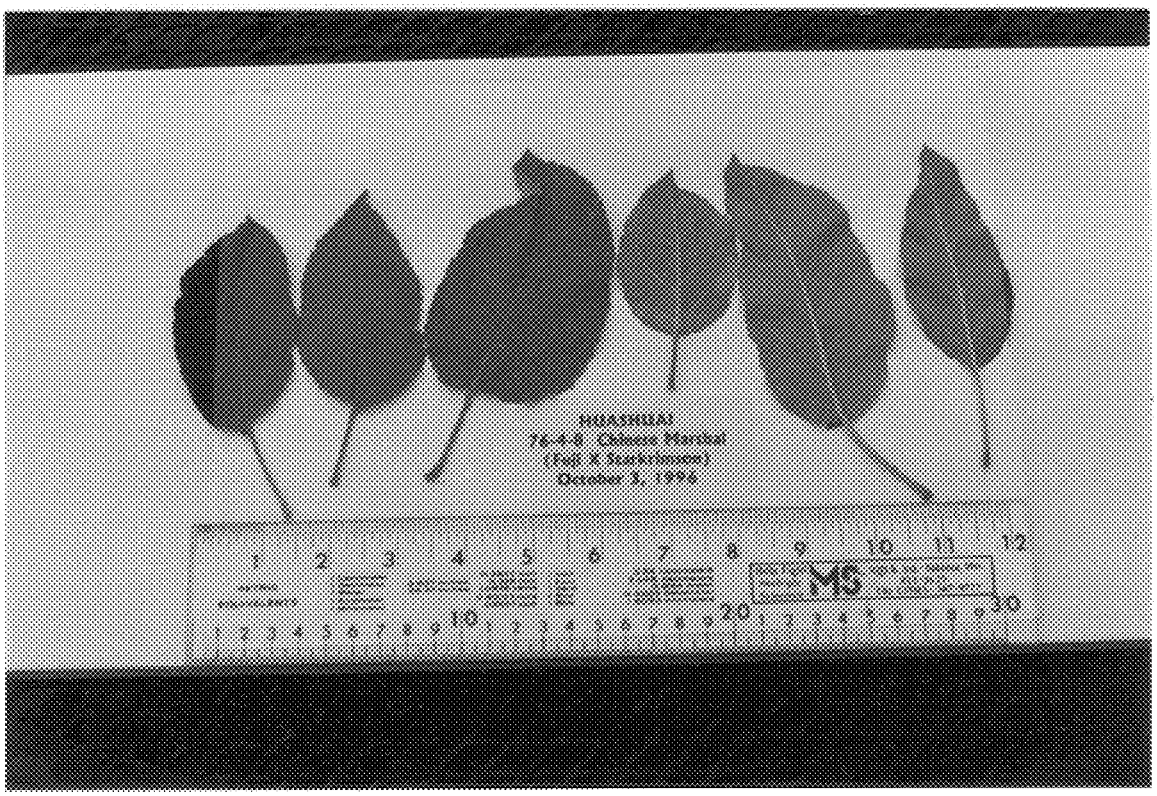
FIG. 3 is a view of both sides of leaves of 'Huashuai' under glass.
Figure 4:
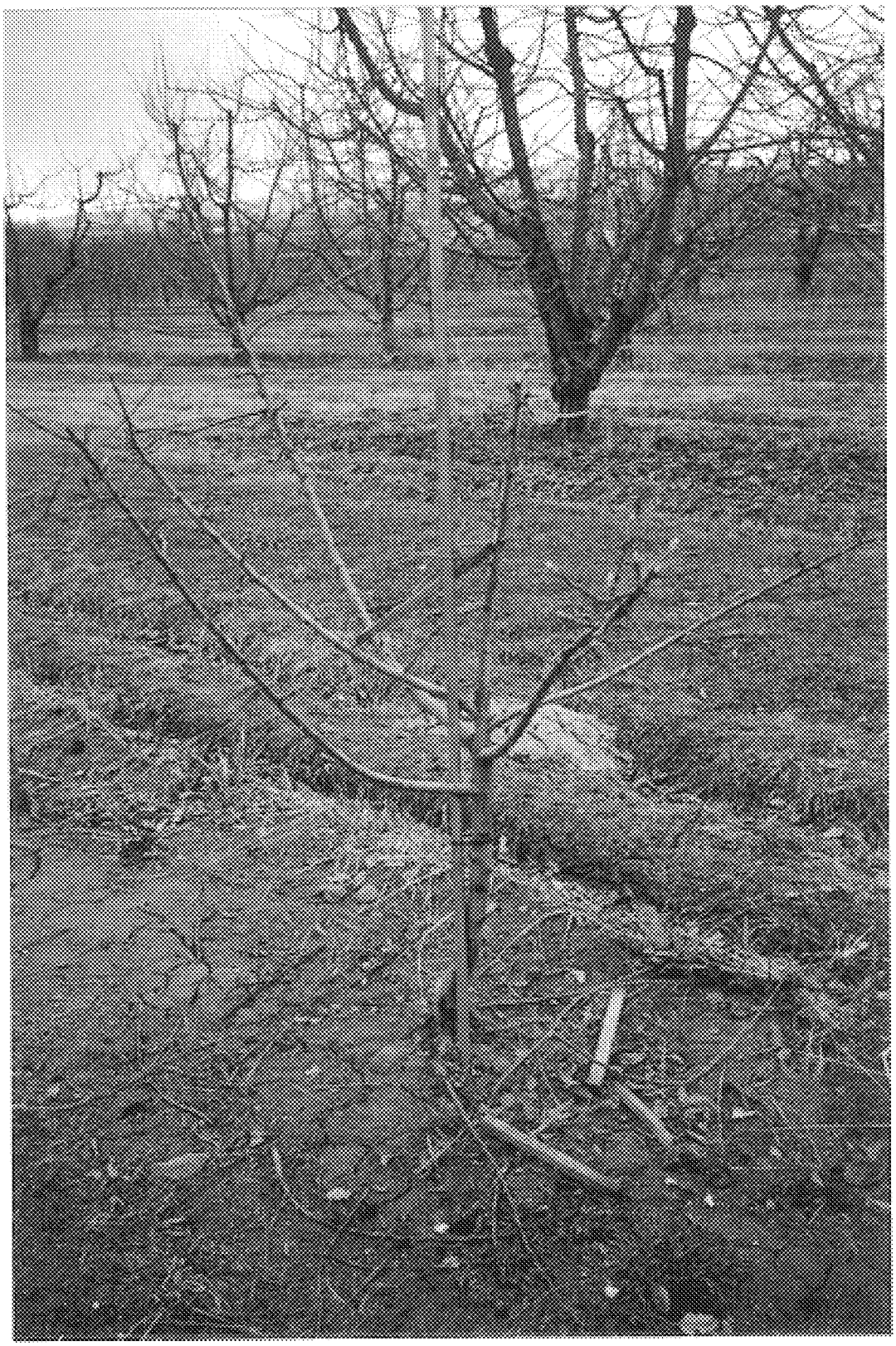
FIG. 4 is a view of a tree of the 'Huashuai' variety that was established as a budded rootstock in 1992 (photograph taken February 1997).
Figure 5:
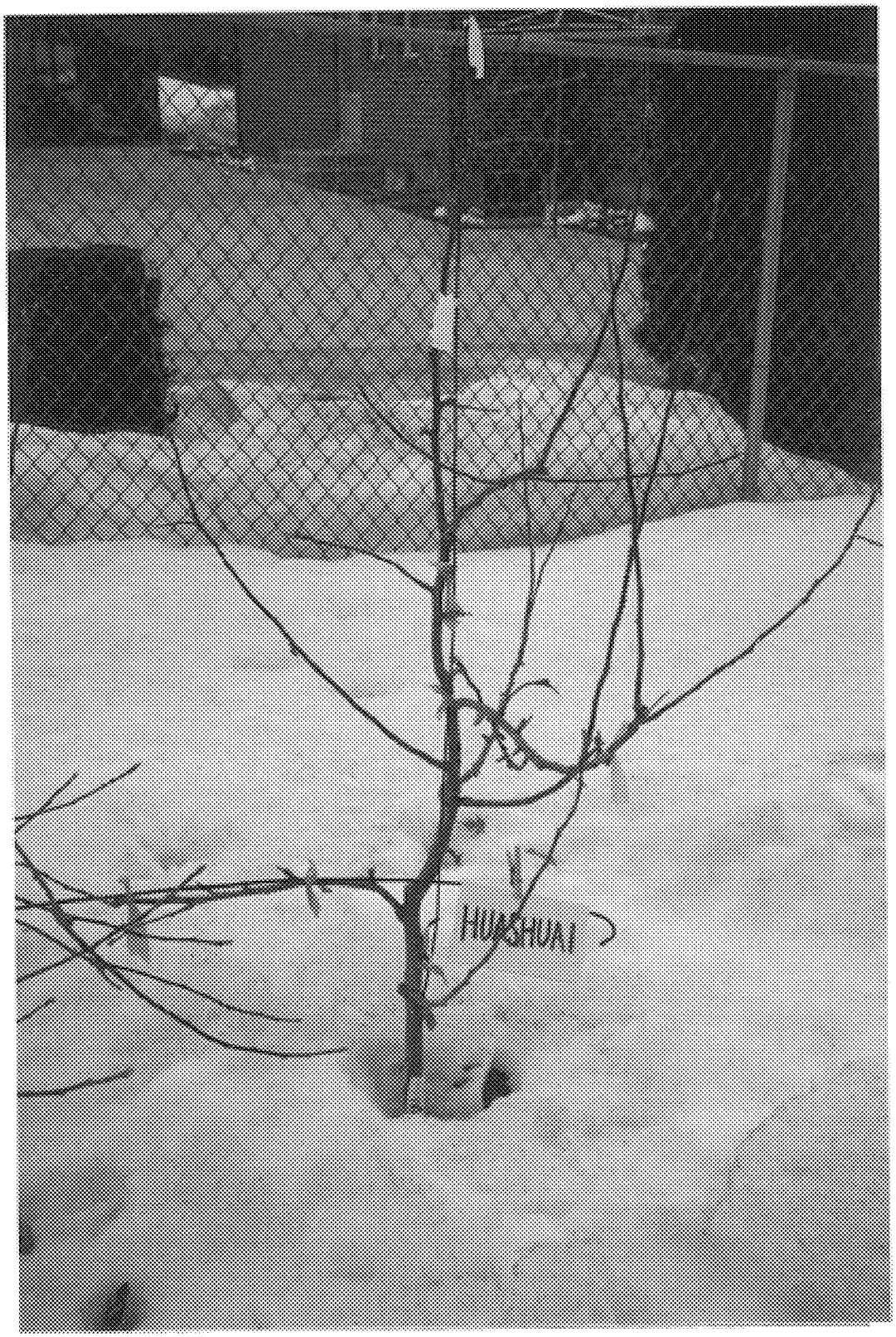
FIG. 5 is a view of a four-year-old tree of 'Huashuai' showing the effect of early bearing of fruit the previous year.
Figure 6:
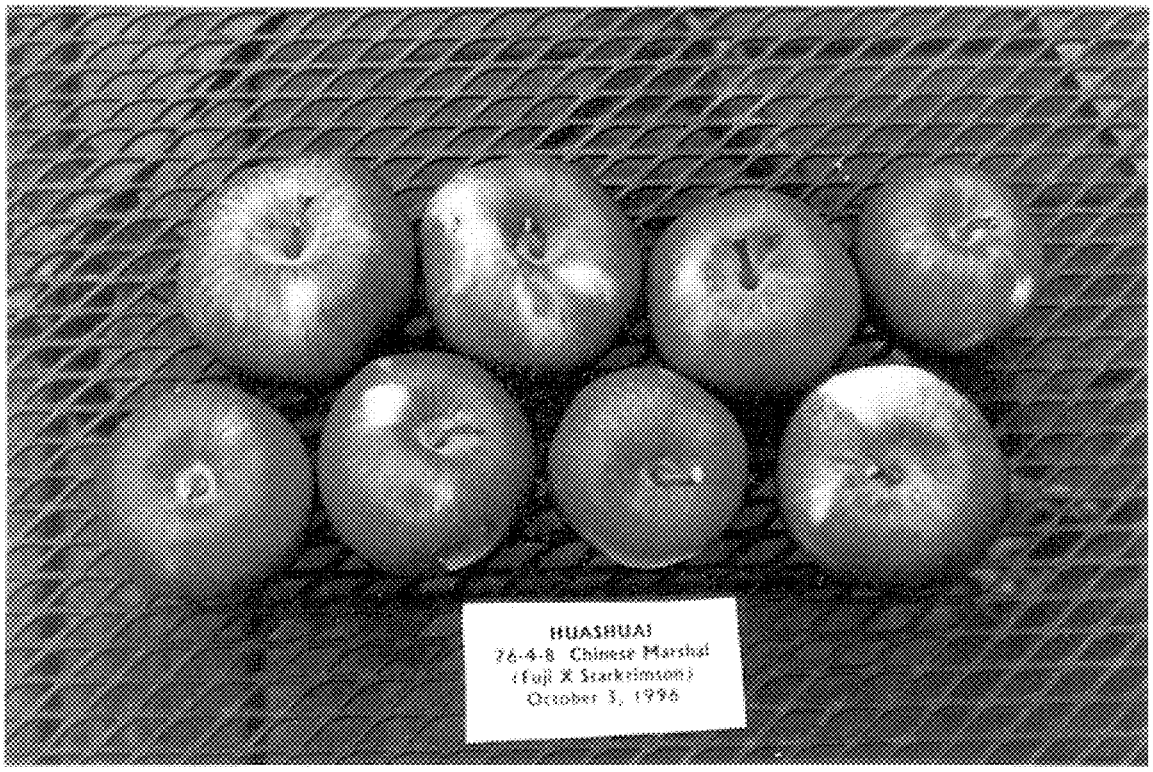
FIG. 6 is a stem-end view of fruit of 'Huashuai'.
Figure 7:
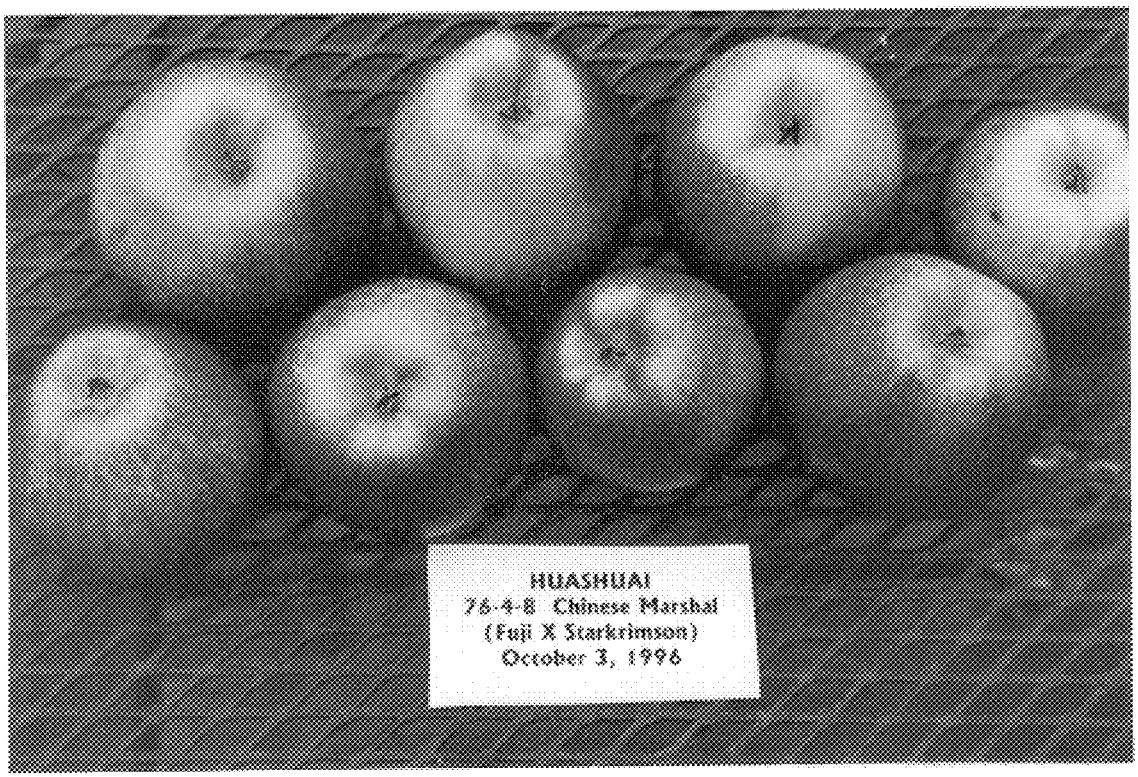
FIG. 7 is a calyx-end view of fruit of 'Huashuai'.
Figure 8:
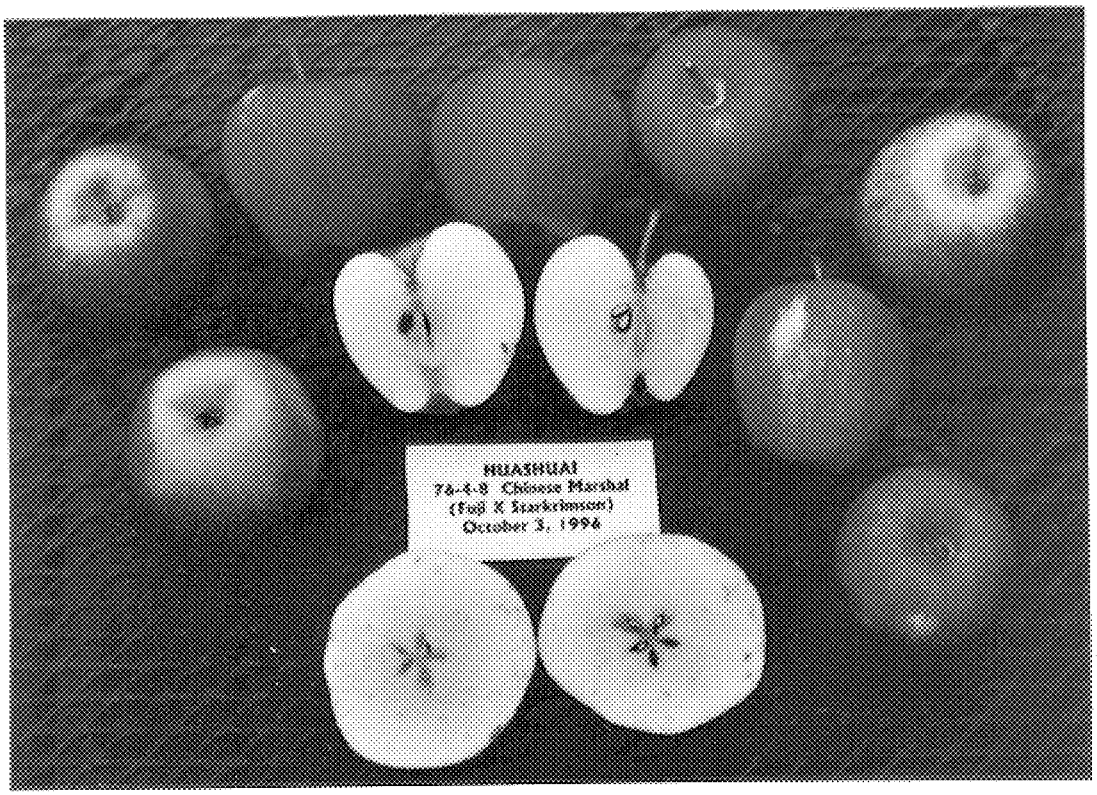
FIG. 8 shows stem-end, calyx-end, side, and sectional views of fruit of 'Huashuai'.

*Habit.*—Standard tree type with spreading branches (due to early and heavy fruit production of fruits, FIGS. 4 and 5).

*Lenticels.*—Small, inconspicuous, and light buff to yellow color.

Leaves:

*Size.*—3.5 to 4.0 cm wide, 6.0 to 7.0 cm long.

*Shape.*—Ovate to oblong with sinuate, serrate margins.

*Color.*—Upper side: Dark green (like R.H.S. 139A) with prominent veins. Underside: Like R.H.S. 139A, but lighter than the upper leaf surface. Covered with a medium buff/green pubescence.

*Margin.*—Fine to medium serrations.

*Petiole.*—2.0 to 3.0 cm long, color variable, typically green.

Flower: Tight, deep red buds (somewhat like R.H.S. 63A) opening to a blossom with white petals (whiter than R.H.S. 155D) tinged with a slight pink blush, similar to 'Bisbee'. Faint or slight fragrance typical of apple trees. Blooms midseason (2–3 days after 'Huaguan' (U.S. Plant Patent application Ser. No. 08/982,985) over a period of 8–14 days in most years. Although variable with location and weather conditions in Selah, Wash., in 1997, first bloom of 'Huashuai' was observed on April 13$^{th}$ and peak bloom was observed from May 2$^{nd}$ to 5$^{th}$. The bloom has five carpels, typical of 'Bisbee' apple trees and usual ovaries. Insofar as observed, the pollen, styles and other reproductive parts are like those typical of 'Bisbee' apple trees.

Fruit:

*Size.*—Variable, typical 6 to 7 cm diameter.

*Shape.* —Conical to round or ovate, with five prominent points on the calyx end, similar to 'Bisbee'. Depending on seed count, may become slightly lop-sided.

*Stem cavity.*—Deep (1.0 to 1.5 cm).

*Basin cavity.*—Deep (1.0 to 1.5 cm), with the five points found, for example, on 'Bisbee' but less pronounced than on 'Bisbee'.

*Stem.*—Medium slender. Length varies from medium (2.0 cm) to long (3.0 to 3.5+ cm), generally shorter than stems of 'Fuji' (up to 3.5+ cm).

*Calyx.*—Inconspicuous, generally tightly closed. Calyx bowl deeper than 'Fuji'.

*Carpels.*—Five, tightly clustered.

*Skin.*—Smooth, good wax layer that can produce a bright shine. Not russet prone.

*Ground color.*—Greenish yellow to golden yellow from first to last picking (like R.H.S. 145B, although yellows with maturity).

*Color markings/overcolor.*—Very attractive pink to red blush made up of fine bright crimson red stripes (like R.H.S. 53B).

*Lenticels.*—Numerous, very inconspicuous.

*Color of lenticels.*—Buff to yellow.

*Flesh.*—Fine, crisp and very juicy. Color: creamy white, similar to 'Fuji', more whitish than 'Huaguan'. Flavor: Rated high, sweet with low acidity (less acidity than 'Fuji'), with a mild distinguishing aroma.

*Quality.*—Very good. Rated better than 'Fuji', in China because of long storage and shelf life and market acceptance.

*Core.*—Bundle area is 2 cm wide and up to 6 cm long. Bundles: Five. Core lines: Well defined. Calyx-tube: Short and tightly closed. Cell walls: Thinner than 'Bisbee'.

*Seeds.*—Number per cell: Maximum of four, usually fewer in a poor pollination year. Length: 0.5 to 0.75 cm. Breadth: 0.25 cm. Color: Black.

*Use.*—A superior fresh eating cultivar, excellent for pies, sauce and juice.

*Keeping quality.*—Very good. Fruit remains firm and crisp at room temperature for seven to ten days.

*Storage.*—Up to six months in common storage and a full year in CA.

Production: Moderate, similar to the both parents.

Pollination: Diploid, requiring pollen of another diploid variety blooming in mid-season such as 'Huaguan', 'Bisbee', or 'Fuji'.

Resistance to insects and disease: Mildly susceptible to mildew and fireblight. Very susceptible to scab. Vulnerable to all insect pests of apple.

I claim:

1. A new and distinct variety of apple tree substantially as herein shown and described.

* * * * *